United States Patent [19]
Schmidt

[11] Patent Number: 5,205,813
[45] Date of Patent: Apr. 27, 1993

[54] CEPHALIC AND CERVICAL SUPPORT APPLIANCE

[76] Inventor: Shawn M. Schmidt, 812 Tipperary Dr., Papillon, Nebr. 68046

[21] Appl. No.: 753,925

[22] Filed: Sep. 3, 1991

Related U.S. Application Data

[63] Continuation-in-part of Ser. No. 461,815, Jan. 8, 1990, abandoned.

[51] Int. Cl.$^5$ .............................................. A61F 5/00
[52] U.S. Cl. ...................................... 602/17; 602/18; 128/97.1
[58] Field of Search .................. 602/17, 18; 128/97.1; 2/44, 45

[56] References Cited

U.S. PATENT DOCUMENTS

| Re. 32,219 | 8/1986 | Garth . | |
|---|---|---|---|
| 2,736,314 | 2/1956 | Hale . | |
| 2,904,040 | 9/1959 | Hale . | |
| 3,343,532 | 9/1967 | Zumaglini . | |
| 3,921,626 | 11/1975 | Neel . | |
| 4,043,325 | 8/1977 | Ochs et al. . | |
| 4,141,368 | 2/1979 | Meyer . | |
| 4,194,501 | 3/1980 | Watt . | |
| 4,204,529 | 5/1980 | Cochrane . | |
| 4,219,193 | 8/1980 | Newman | 602/17 X |
| 4,515,153 | 5/1985 | Calabrese . | |
| 4,576,150 | 3/1986 | Auracher . | |
| 4,677,969 | 7/1987 | Calabrese . | |
| 4,708,129 | 11/1987 | Pujals, Jr. . | |
| 4,712,540 | 12/1987 | Tucker et al. . | |
| 4,736,736 | 4/1988 | Moers et al. | 602/18 |
| 4,854,306 | 8/1989 | Pujals, Jr. . | |
| 4,886,052 | 12/1989 | Calabrese | 602/18 |
| 5,003,968 | 4/1991 | Mars | 602/17 |
| 5,054,475 | 10/1991 | Calabrese et al. | 602/17 |

Primary Examiner—Richard J. Apley
Assistant Examiner—Linda C. M. Dvorak
Attorney, Agent, or Firm—John A. Beehner

[57] ABSTRACT

A cephalic and cervical support apparatus for immobilization and traction of the cervical rachis including a semirigid, flexible unitary shell having a facial opening and upper, middle and lower sections. The upper section substantially conforms to a wearer's head and has a forehead strap which extends in a substantially horizontal direction across the wearer's forehead. The middle section substantially conforms to a wearer's neck area, encircling the neck area, and having a division in the shell in the submandibular region. The lower section substantially conforms to the wearer's upper shoulder, back and chest area, and has a division connected to the division in the middle section which allows the shell to be opened for installation on a wearer. The division can be releasably closed by a fastening device, and the support apparatus can be held on a wearer by engagement of a pair of arm straps. A structural combination of three curves, the convex curve formed by the joining of the three sections, the downwards facing lower concave curve which conforms to the wearer's shoulders and the middle concave curve conforming to the wearer's neck, results in greater rigidity of the shell even with the use of a relatively lightweight structural material.

21 Claims, 13 Drawing Sheets

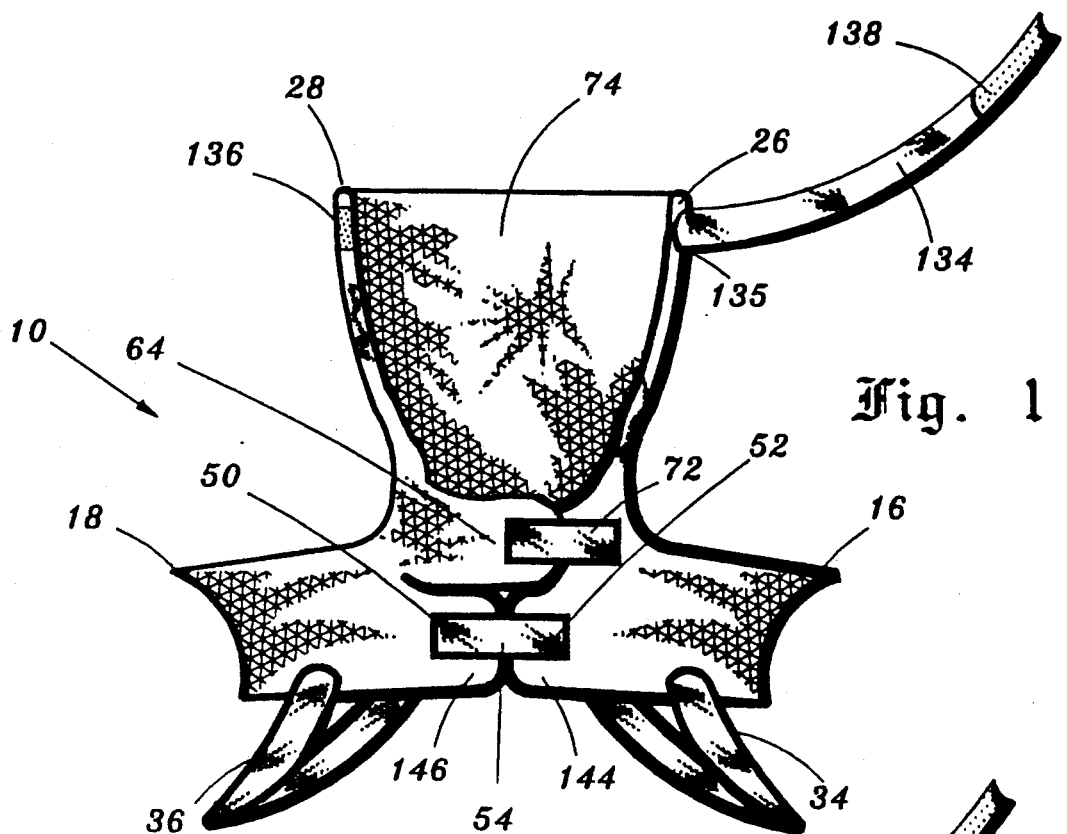
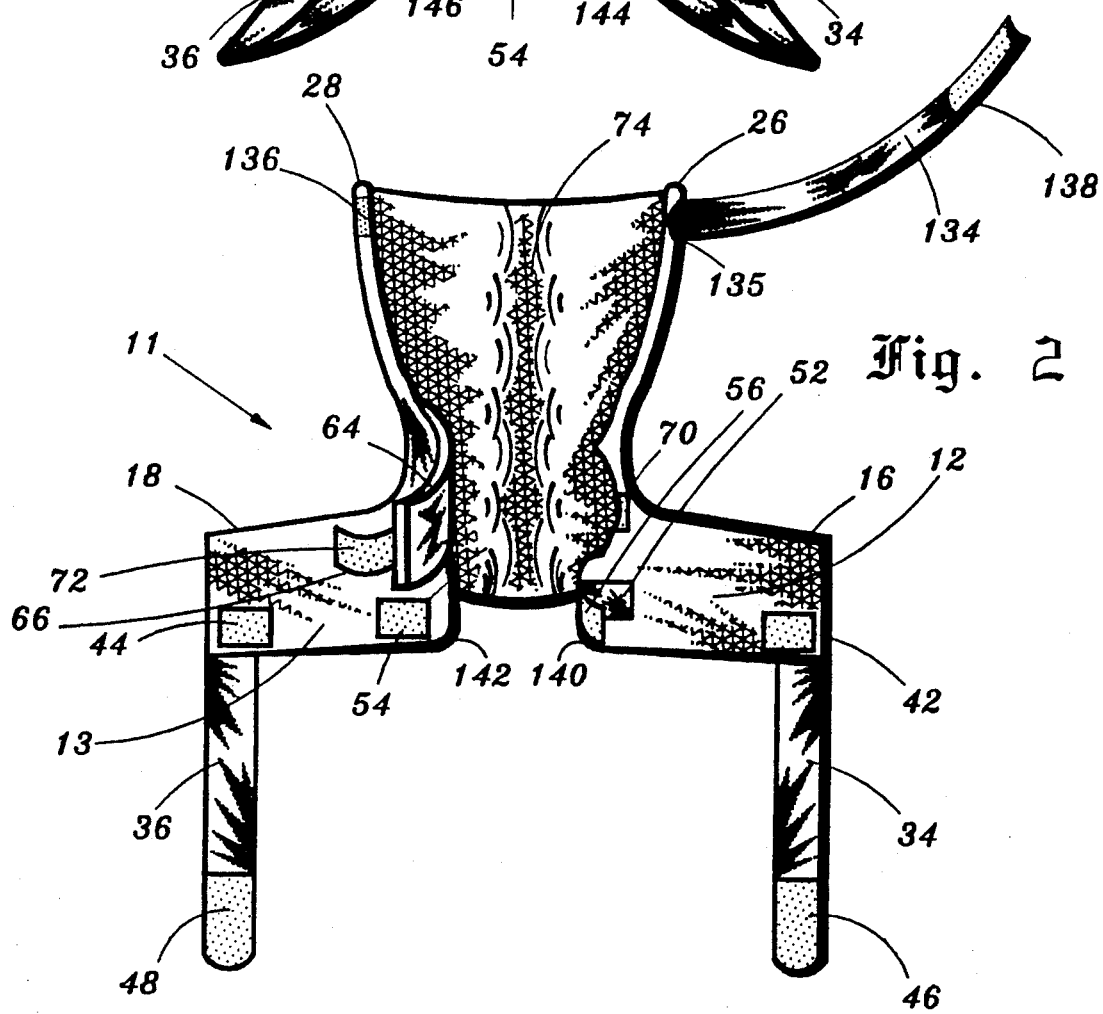

CEPHALIC AND CERVICAL SUPPORT APPLIANCE

CROSS REFERENCE TO RELATED APPLICATION

This patent application is a continuation-in-part of U.S. patent application Ser. No. 461,815, filed on 8 Jan. 1990, now abandoned.

BACKGROUND OF THE INVENTION

The present invention is directed generally to an improved anatomical support or orthopedic appliance and more particularly to an orthopedic appliance adapted for immobilizing the human cephalic, cervical, and upper thoracic vertebrate.

It is often necessary to transport injured individuals to trauma centers. On many occasions it is not known whether these individuals have sustained cephalic or cervical injuries that may be exacerbated should the traumatized individual be moved. Additionally, atlas, axis, or other vertebral fractures of the cervical rachis, often produce jagged edges of bone capable of severing the spinal chord or the cervical vascular supply to the brain.

Therefore, a method of quickly and safely immobilizing the cervical rachis of those with potential head and neck injuries has long been an object of those skilled in both transporting and administering emergency medical attention.

The saving of even a few seconds in the preparation and transportation of an injured individual can mean the difference between life and death. Since it is often necessary to immobilize the cervical rachis prior to such transportation, orthopedic appliances adapted for such use must be capable of safe and rapid placement on a traumatized individual.

There are several prior art devices designed to immobilize the cervical rachis. However, these devices either require that an injured individual be moved unnecessarily, or are difficult and time consuming to position on a traumatized individual.

For example, Hale, U.S. Pat. Nos. 2,736,314 and 2,904,040 teach the construction of cervical braces that are difficult and unsafe to install and require movement of the head, neck and shoulders to position the appliance on a traumatized individual.

Other multiple piece braces have the same inherent problems: Pujals, U.S. Pat. No. 4,708,129; Calabrese, U.S. Pat. No. 4,677,969; Watt, U.S. Pat. No. 4,194,501; Meyer, U.S. Pat. No. 4,141,368; and Ochs, et al., U.S. Pat. No. 4,043,325.

Other prior art devices such as Tucker, et al., U.S. Pat. No. 4,712,540, provide a single point of attachment, but require the traumatized neck to support itself.

Likewise, at the discretion of an emergency trauma specialist, it is often necessary to place an individual recovering from a cranial, mandible, or cervical injury in an extended state of traction. Prior art devices are available for such use, however, these devices are heavy, cumbersome, and uncomfortable.

Further, it is often desirable to protect convulsion prone patients from head or neck injuries that often occur during seizures. In addition, it is often desirable to maintain the cervical rachis of a comatose patient in a neutral position so as to prevent damage to the rachis and surrounding tissue.

Another problem encountered in using prior art devices equipped with forehead straps is that the forehead straps often rest at an upward angle, i.e. the center of the strap rests higher on the forehead than the ends of the strap. This can cause undesirable downward vertical pressure on the spine, thus exacerbating the spinal injury.

Yet another problem encountered in using prior art devices is that they tend to be heavy and bulky, using heavy plastics in their construction to supply the necessary degree of rigidity for immobilization of the cervical rachis. This results in discomfort for the wearer, which worsens during extended wearing. Therefore, there is a real need for a relatively lightweight cervical rachis immobilization device.

A primary object of the invention is to provide an improved cephalic and cervical support.

Another object of the invention is to provide a support that utilizes the thoracic cavity as a foundation to support the head and neck.

Another object of the invention is to provide a support that is easy to position on an injured patient.

Another object of the invention is to provide a support that is durable and rugged in construction.

Another object of the invention is to provide a support that is comfortable to wear.

Another object of the invention is to provide a support that may be positioned quickly on an injured individual.

Another object of the invention is to provide a support that provides stabilization against flexion, extension, lateral bending, and rotation of the cervical rachis.

Another object of the invention is to provide a support that allows a health care provider access to an injured individual's ears for diagnostic evaluation and potential treatment.

Another object of the invention is to provide a support that allows a health care provider access to an injured individual's anterior neck region.

Another object of the invention is to provide a support that allows a health care provider to artificially ventilate an injured individual.

Another object of the invention is to provide a support that has a forehead securement strap which extends in a substantially horizontal direction across a wearer's forehead thereby substantially eliminating downwards vertical pressure on the spinal column.

Another object of the invention is to provide a support that is relatively lightweight and comfortable to wear for extended periods, yet retains sufficient rigidity to immobilize the cervical rachis.

Finally, another object of the invention is to provide a support that is safe in use and durable in construction.

SUMMARY OF THE INVENTION

The present invention includes a firm yet pliable shell for immobilization and traction of the cervical rachis. The shell opens at the front and includes a back portion formed to be supported on the upper back and extend upwardly past the neck to at least the lambda region of the skull in order to secure the head against rearward movement. The shell also has right and left side portions extending forwardly from opposite sides of the shell back portion to generally conform to the tops of a wearer's shoulders and sides of the wearer's head. The right and left front portions extend forwardly from the right and left side portions for conforming the shell to the anterior upper chest of a wearer.

The appliance is secured to a wearer by a pair of arm straps extending from the left and right sides of the back portion and under the axilla to the left and right sides of the front portion respectively.

The left and right sides of the front portions are releasably and adjustably secured together by straps in order to draw the back and side portions into engagement against the head of a wearer. An additional strap is provided to releasably and adjustably secure the neck stabilizer to opposite front portions so that the appliance conforms to the full circumference of the wearer's head to substantially fix the position of the wearer's head against movement.

In reference to FIGS. 16-25, the following summary describes the present invention as including a semirigid, flexible unitary shell for immobilization and traction of the cervical rachis. The shell opens at the front and includes a facial opening and upper, middle, and lower sections.

The upper section is formed to substantially conform to a wearer's head, extending upwards along the rear of the head to a point above the base of the wearer's occipital bone. The front top edges of the upper section are adjacent the upper portion of the wearer's forehead and substantially conform to the sides of a wearer's head.

The middle section is formed to substantially conform to a wearer's neck area, encircling the wearer's neck and having a division in front to allow the shell to be placed on a wearer. The division extends downwards from the jaw area to the lower section.

The lower section is formed to substantially conform to a wearer's upper chest and shoulder and to rest thereon. A division is formed in the front face of the lower section, extended horizontally, then vertically downwards substantially parallel to the division in the middle section, thus forming a Z-shaped division to allow the shell to open.

The upper, middle, and lower sections join to form a substantially concave joining curve along the sides and rear of the shell.

To secure the support apparatus to a wearer a pair of arm straps are connected to and extend between front and back portions of the lower section, one strap on each side of said lower section, and adjustable and releasable to secure the support on a wearer. The arm straps pass underneath the arms and are reattached to the opposite portion of the lower section.

A forehead strap further secures the support apparatus on a wearer. The forehead strap is releasably and adjustably mounted on the upper section and extending between the upper opposite sides. The forehead strap may be placed across the forehead of a support wearer and secured to further prevent movement of the spinal area. Importantly, the forehead strap is designed to fit on and across the wearer's forehead in a substantially horizontal holding position, thus substantially eliminating downward vertical pressure on the spine of the support apparatus wearer, pressure which could possibly cause additional injury to the spine.

Lastly, the front division can be releasably and adjustably closed and secured by a fastening means such as a hook and loop fastener, so that a range of differently sized wearers may be accommodated.

BRIEF DESCRIPTION OF THE DRAWINGS

FIG. 1 is a front view of a preferred embodiment of the Cephalic and Cervical Support Appliance 10 showing the axillary straps in an engaged position;

FIG. 2 is a front elevational view of a second embodiment having axillary straps being attached to the center back portion of the appliance 11 and showing the securement straps in a disengaged position;

DESCRIPTION OF THE PREFERRED EMBODIMENT

Figure 6:
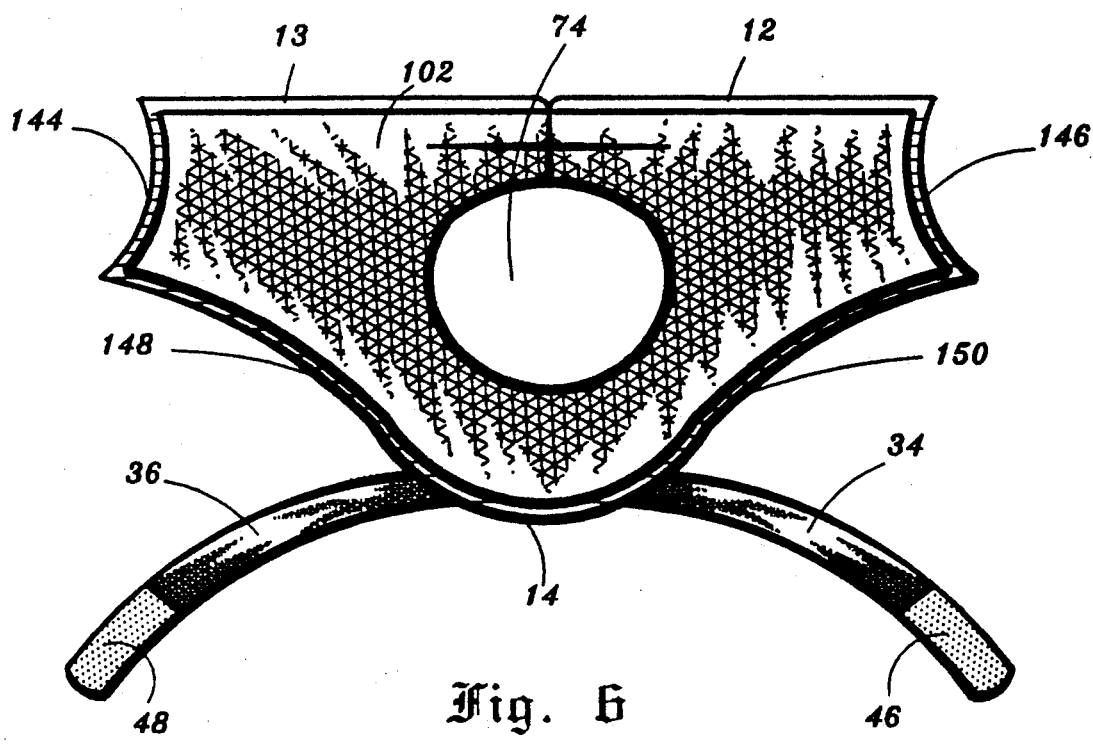
FIG. 6 is a bottom elevational view illustrating the outline of the upper thoracic cavity formed by the appliance.
Figure 7:
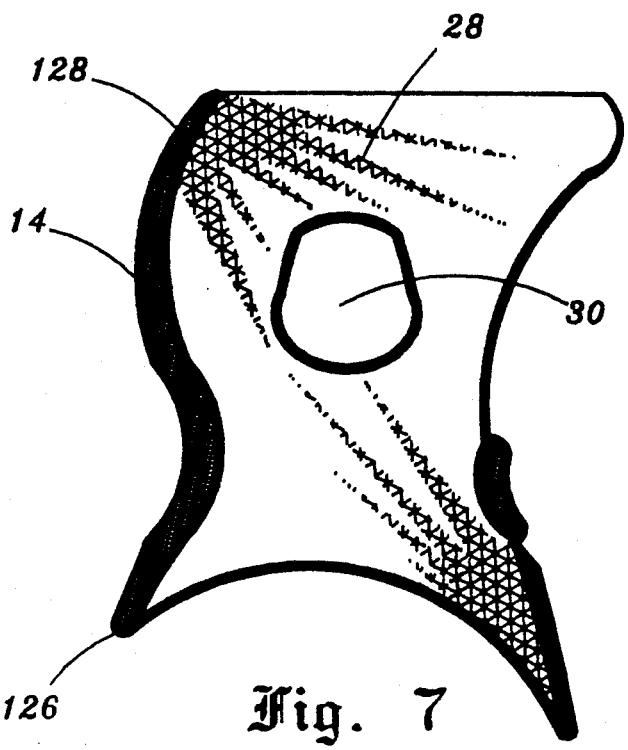
FIG. 7 is a side cross-sectional view showing the right ear portal of the appliance.
Figure 8:
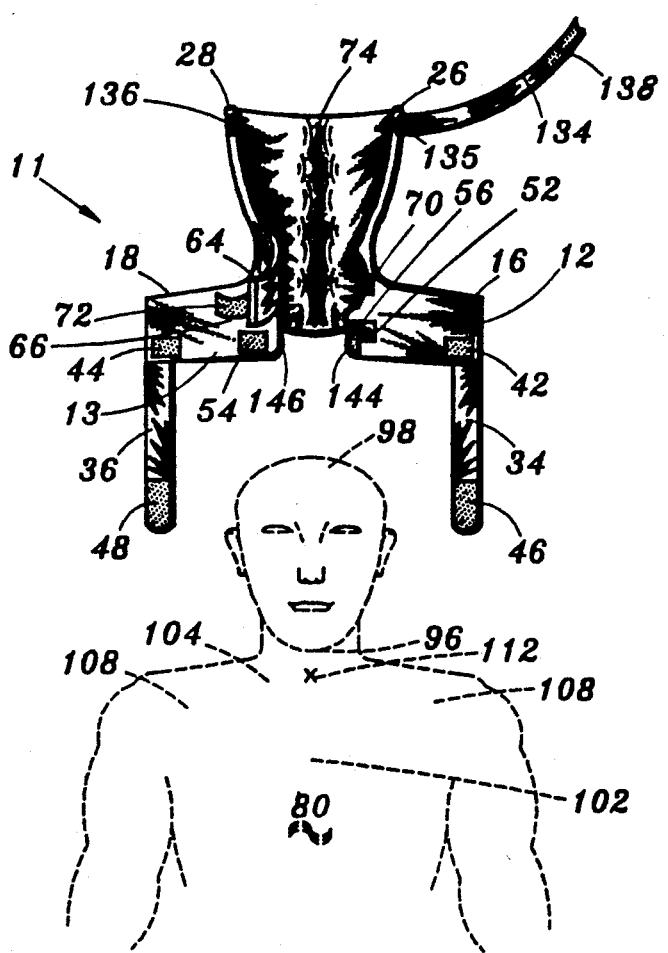
FIG. 8 is a front elevational view of the FIG. 2 embodiment positioned for placement on an accident victim.
Figure 9:
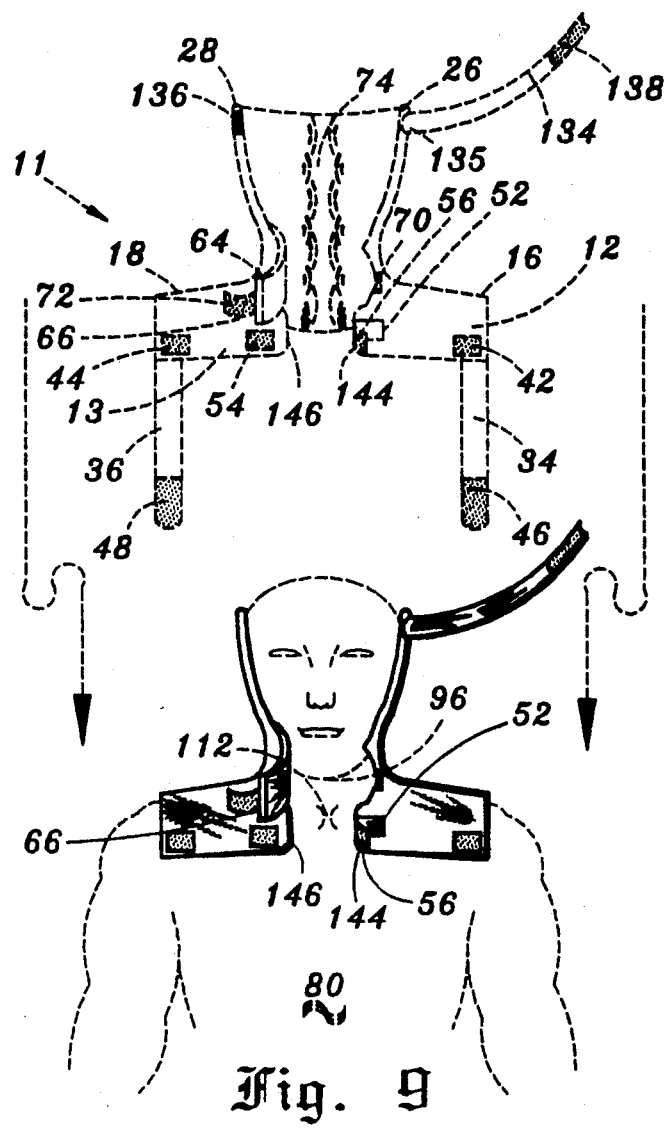
FIG. 9 is a front elevational view of the FIG. 2 embodiment positioned above and ready to be placed from the posterior to the anterior onto an accident victim.
Figure 14:
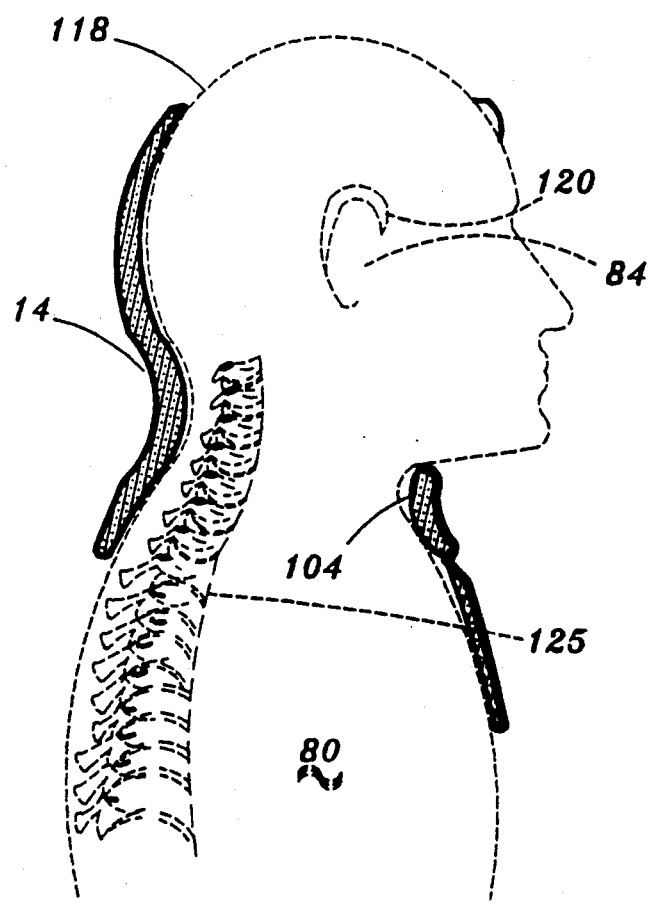
FIG. 14 is a cross-sectional side view of a preferred embodiment positioned on an accident victim and showing an abbreviated internal anatomy of the cephalic and cervical regions.
Figure 15:
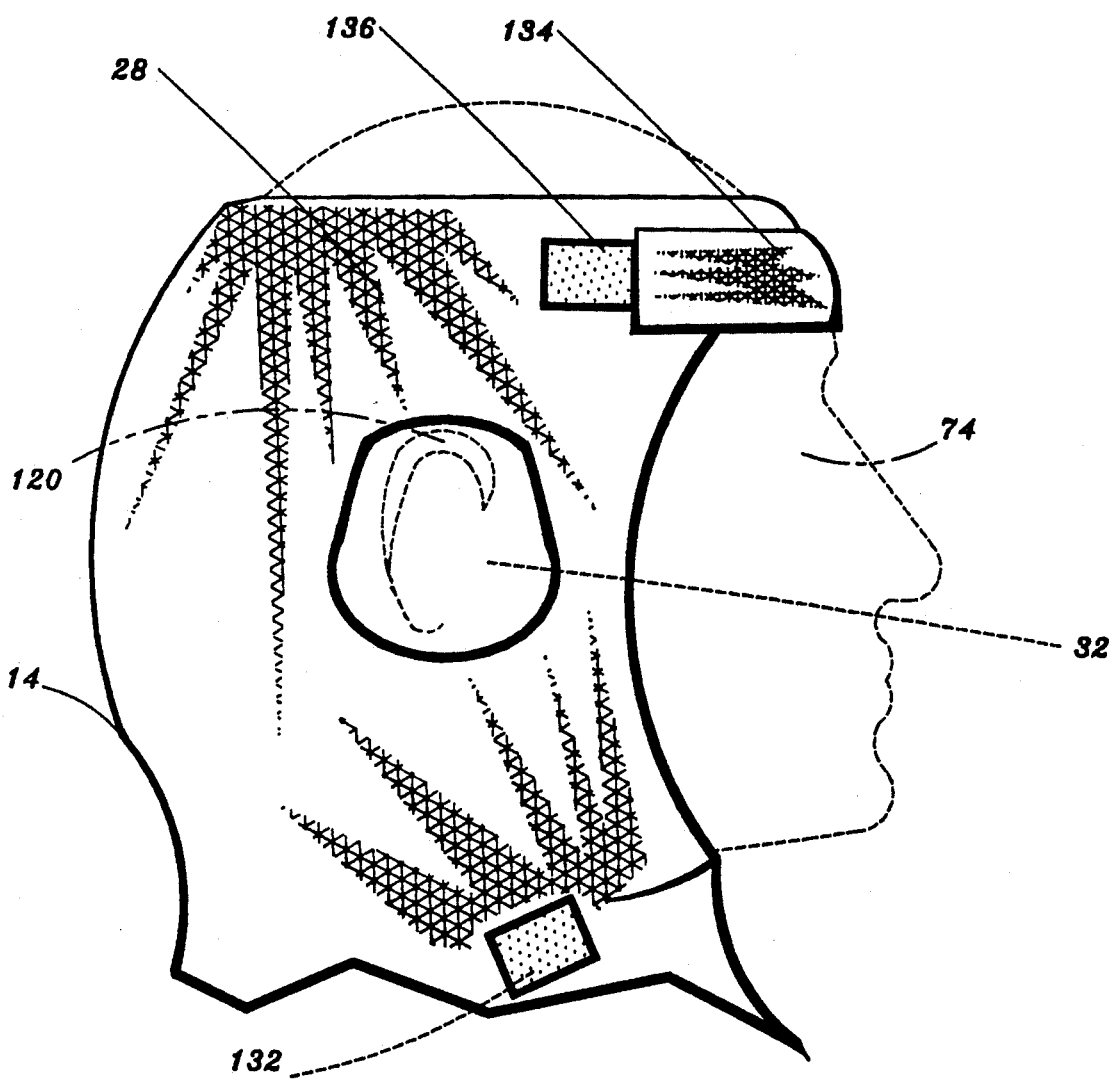
FIG. 15 is a partial sectional side view showing the right ear through the portal of a preferred embodiment.
Figure 16:
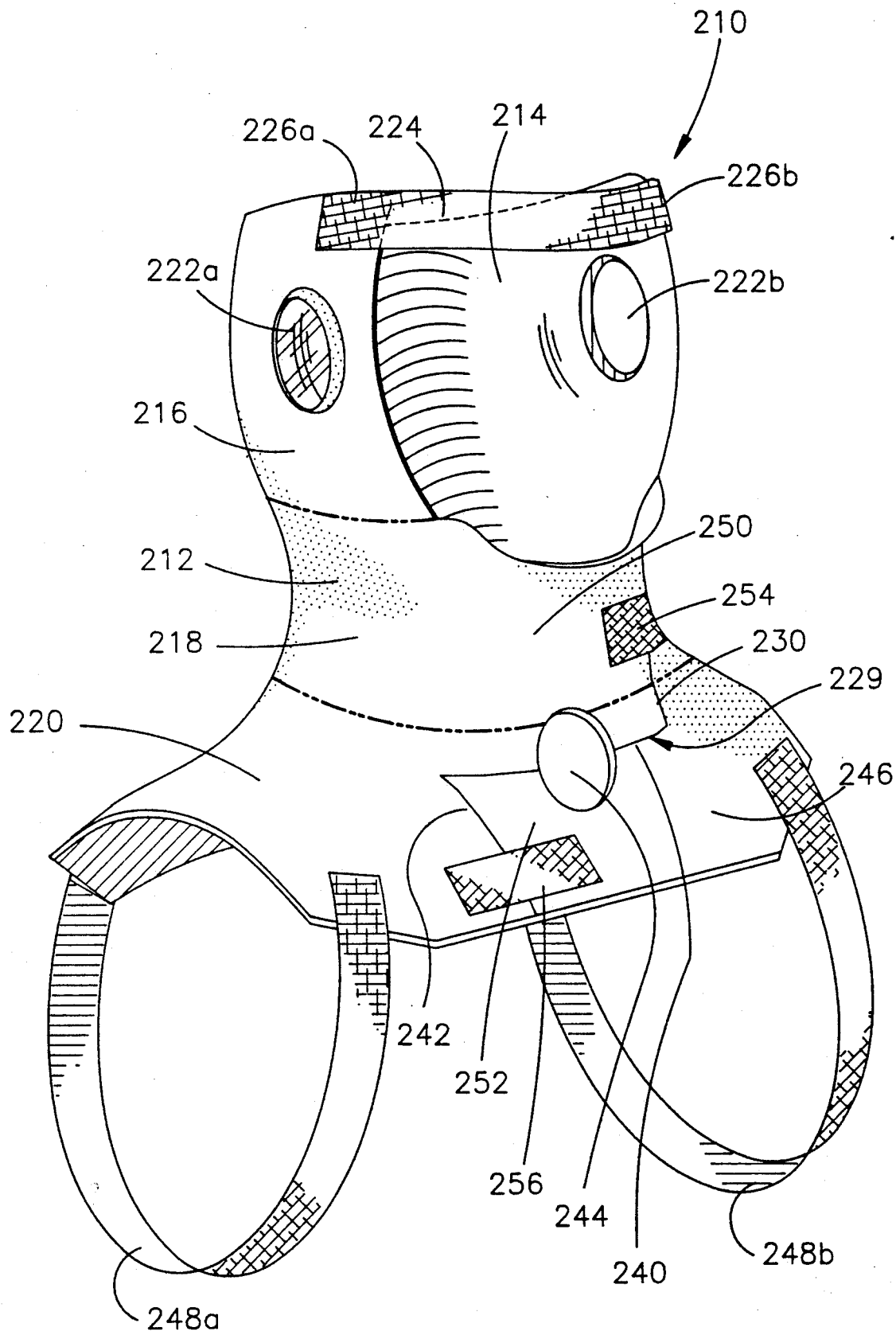
FIG. 16 is a perspective view of an alternative embodiment of the invention showing the facial opening, arm straps and other features of the invention.

The Cephalic and Cervical Support Appliance of the present invention is illustrated in two embodiments 10 and 11. The embodiment of FIG. 1 is further depicted in FIGS. 3, 4, 5, 6, 10, 11, 12, and 13 and is designated by the numeral 10. The second embodiment is shown in FIGS. 2, 8, and 9. FIGS. 7, 14, and 15 are generic to both embodiments and illustrate the appliance in cross-sectional views.

The two embodiments (10 and 11) differ in the placement of the back portion 14 attachment points 38 and 40 (FIGS. 2 and 4) of the axillary straps 34 and 36. The appliance 10 has the axillary straps 34 and 36 fixed at the lower center 15 of the back portion 14, while the appliance 11 has the axillary straps 34 and 36 fixed on the back left and right shoulder portions 16 and 18.

The appliance of both embodiment 10 and 11 includes a firm yet pliable bilayer shell of a polyurethane closed cell foam 126 covered by an easy to clean pliable synthetic polymer 128 (FIG. 7). As shown in FIGS. 2 and 6 the shell opens at the front (left and right front portions 12 and 13), and includes an opening 74 (FIG. 8) adapted so as to leave the facial area unobstructed by the installed appliance 10 or 11.

Included in the preferred embodiments is a back portion 14 formed to be supported on the upper posterior of the thoracic cavity. The back portion 14 extends upwardly past the neck to the lambda 118 region of the skull (FIG. 14). The thickness of the back portion increases from about 2.0 centimeter at or near point 15 to about 3.0 centimeters so that the thickness of the shell is greatest from the base of the neck to the upper extent of the back portion 14.

Figure 3:
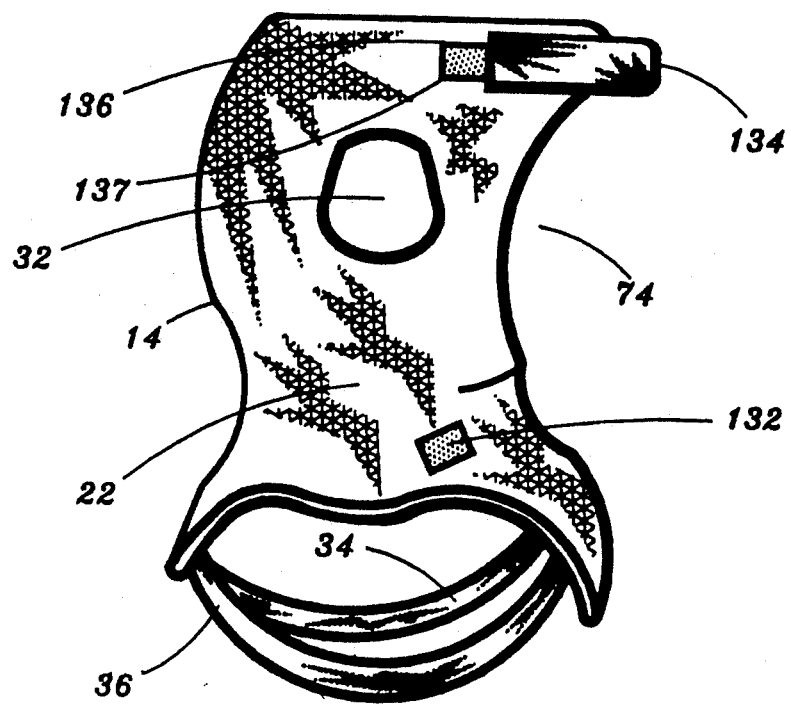
FIG. 3 is a side elevational view of the FIG. 1 embodiment showing the right ear portal and the anterior cervical flap retainer hook fastener for locking the flap in an open position.
Figure 4:
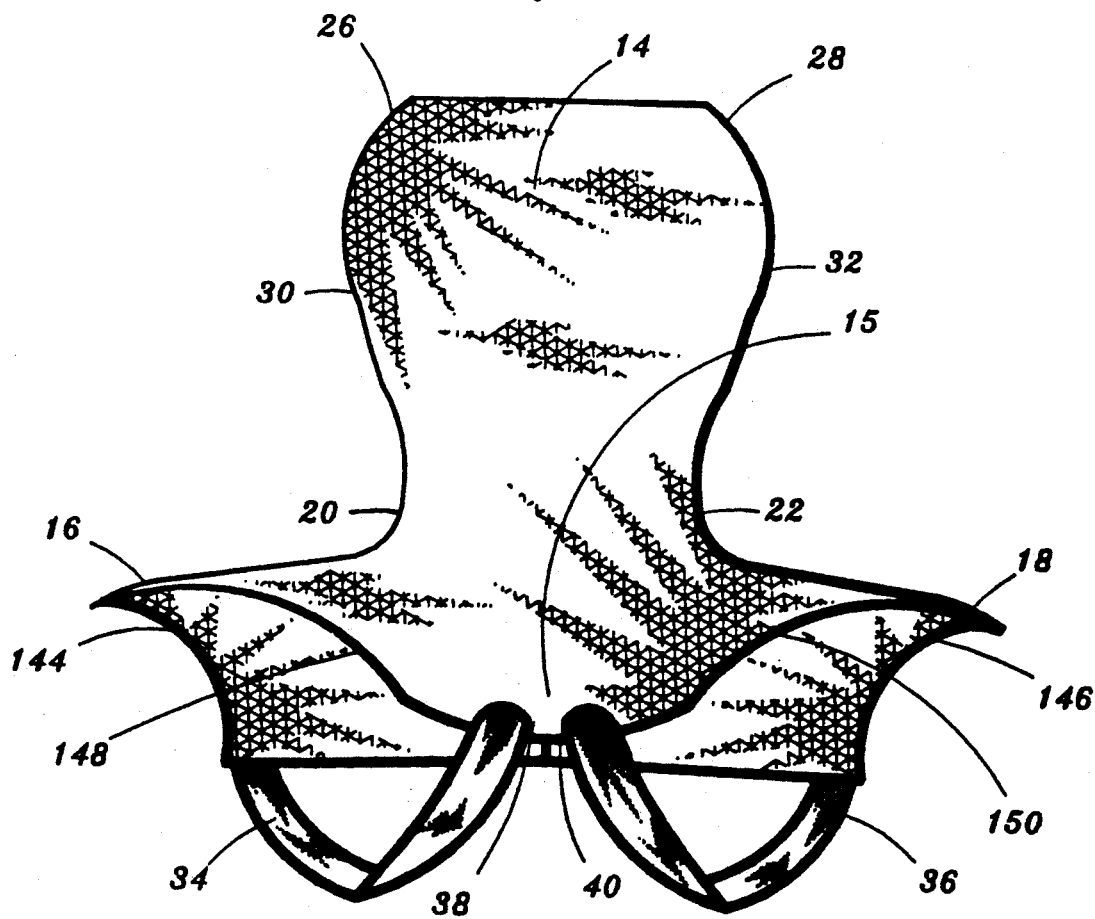
FIG. 4 is a rear elevational view of the FIG. 1 embodiment showing the left and right arm straps and their attachment points.
Figure 5:
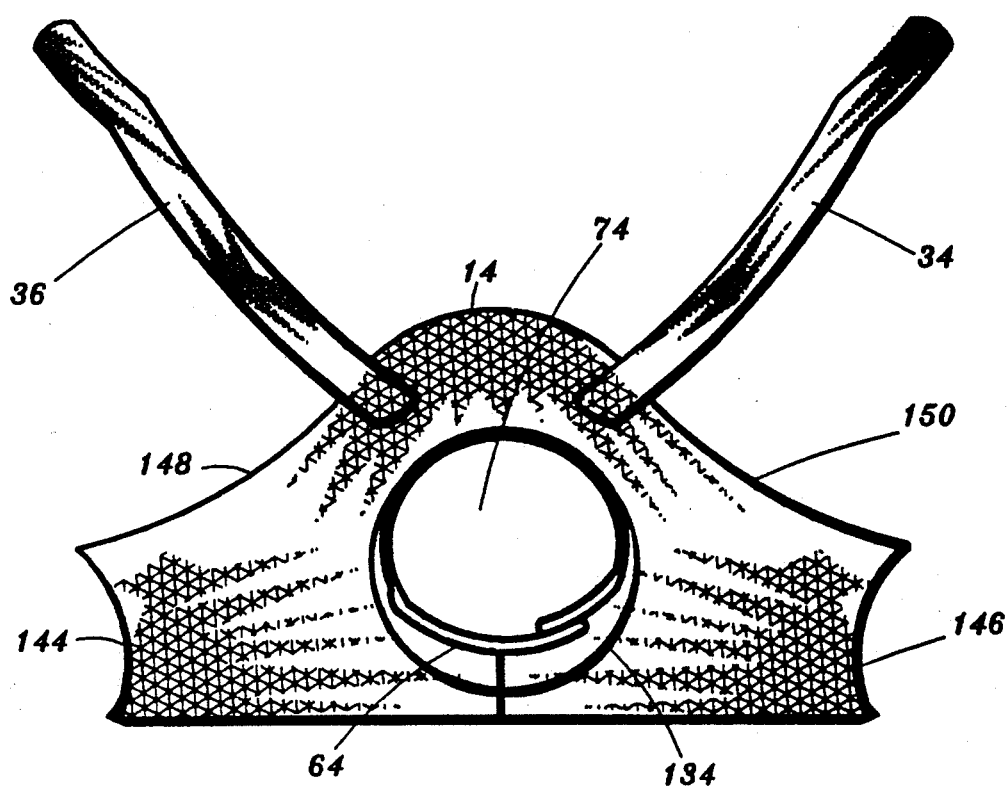
FIG. 5 is a top elevational view showing the head and face openings of the appliance.

The shell also includes left and right side portions extending forward from opposite sides of the back portion 14. The left and right side portions include left and right side shoulder portions 16 and 18, left and right side neck portions 20 and 22, and left and right side head portions 26 and 28 (FIG. 4).

The left and right side head portions 26 and 38 of the shell extend upwardly to approximately 5.5 centimeters above the helix 120 of each ear 84 (FIG. 14). The left and right side head portions 26 and 28 of the shell have ear portals 30 and 32 respectively. The ear portals 30 and 32 are of a sufficient dimension to allow a health care provider access to an accident victim's ears 84.

The left and right side head portions 26 and 28 extend forward from the back portion 14 to the sides of a wearer's face so as to sheath and support a wearer's cervical rachis 125 and prevent movement of the head.

The back portion 14 extends upwardly and forwardly to the left and right front portions 12 and 13 to form left and right shoulder portions 16 and 18. So that the shell forms a cavity adapted to be fitted over the upper thoracic cavity 102 of an accident victim 80, the left and right shoulder portions extend at the left and right back from point 15 to the medial border of the scapula 101, and along the left and right front portions from approximately 5.0 centimeters below the jugular notch 112 along the clavicle 108 to the anterior angle of the axial 109.

Figure 10:
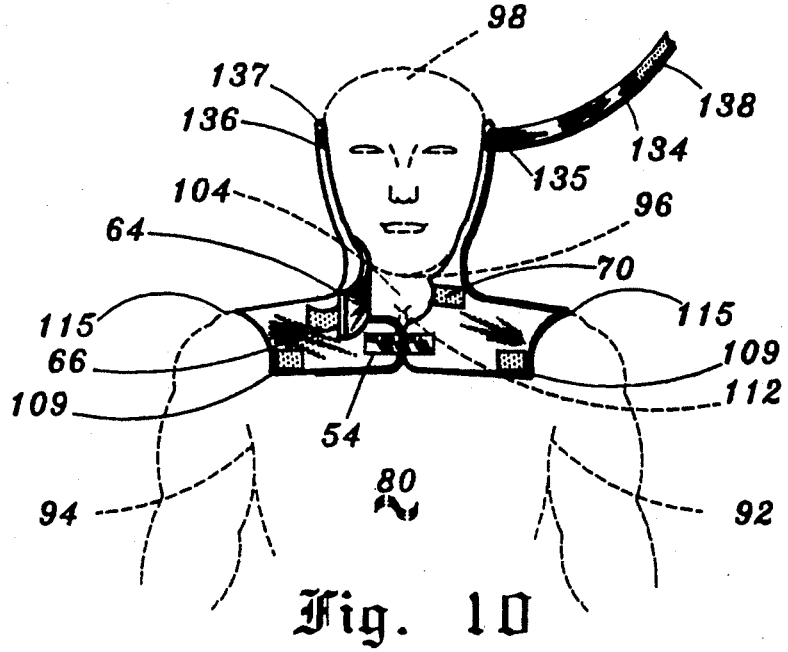
FIG. 10 is a front elevational view of the FIG. 2 embodiment positioned on an accident victim and showing the draw strap securing the front portions of the appliance.

The left and right front edges 140 and 142 of the left and right front portions 12 and 13 are drawn and held together by a draw strap 50 (FIGS. 9 and 10). The draw strap 50 is preferably made from a woven nylon strapping material, and is permanently attached on the left front portion 12 at point 52 (FIG. 8). Sewn or glued to the opposing end of the strap 50 is a portion of loop fastener 56 adapted to be removably secured by a portion of hook fastener 54 attached to the front right portion 13.

So as to draw the left and right front 144 and 146 and left and right back 148 and 150 shoulder portions together a pair of axillary straps 34 and 36 are provided (FIG. 4).

As shown by FIGS. 1 and 2 the axillary straps 34 and 36 may be permanently attached at either point 15 of the back portion 14, or on the left and right sides of the back portion 38 and 40 respectively.

Sewn or glued to the opposing ends of the axillary straps 34 and 36 are portions of loop fasteners 46 and 48. Sewn or glued to the front left and right shoulder portions 144 and 146 are hook fastener portions 42 and 44. The straps 34 and 36 are passed beneath the left and right arms 92 and 94 and are secured by the hook and loop fasteners so as to draw the left and right front (12 and 13) and back 14 portions together. Thus, secured by the axillary straps 34 and 36 a rigid foundation is formed by the shell about a wearer's thoracic cavity 102.

The right front portion 13 forms an anterior cervical flap 64 positioned above the right draw strap hook fastener 54 attachment point. The flap 64 extends to overlap the left front edge 140 so as to cover the anterior cervical region 104 from the mandible 96 to the jugular notch 112.

Permanently attached to the flap 64 at point 68 is a woven nylon strap 66. Sewn or glued to the opposing end of the strap 66 is a portion of loop fastener 72 adapted to be removably secured by a portion of hook fastener 70 attached to the left front portion 12 of the shell. In this way the anterior cervical strap 66 may be used to secure the anterior cervical region 104 and adding further rigidity to the left and right neck portions 20 and 22 of the appliance (10 or 11).

Likewise, the anterior cervical region 104 may be exposed while the appliance (10 or 11) is positioned on an accident victim 80 by drawing the flap 64 to the right so that the strap 66 loop fastener portion 72 may be removably secured by the hook fastener portion 132 (FIG. 3) permanently attached to the right cervical side of the shell 22. Thus, with the flap 64 secured in this position, health care providers may perform tracheotomies or the like.

In order to cause the shell material of the left and right side head portions 26 and 28 to conform to the shape of a wearer's head, and to further secure and immobilize the cervical rachis, a frontal region strap 134 of woven nylon is provided.

The frontal region strap 134 is permanently attached at point 135 on the left head side portion 26. Sewn or glued to the opposing end of the strap 134 is portion of loop fastener 138 for attachment to a portion of hook fastener 136 permanently attached to the right head side portion at point 137. The strap may be drawn across an accident victim's forehead 98 and secured by the strap hook and loop fastener means (FIG. 13).

Figure 13:
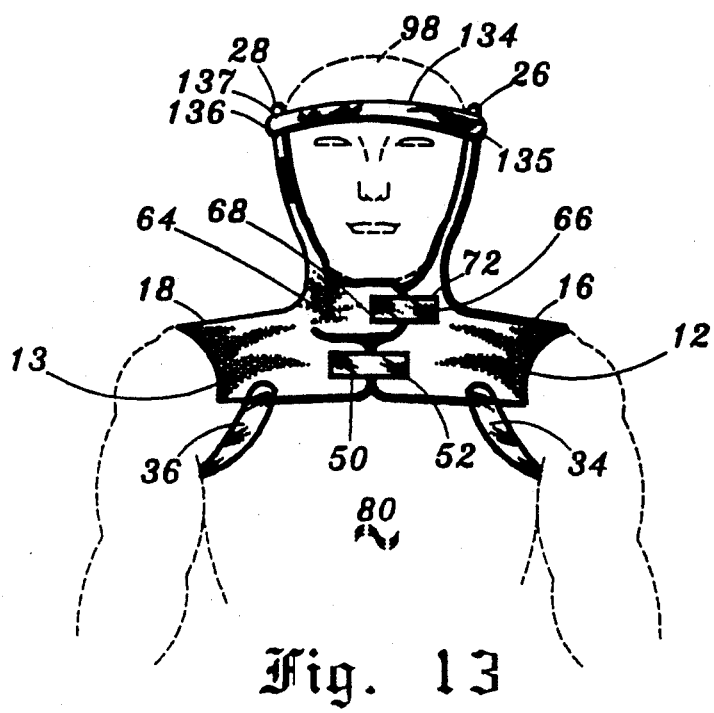
FIG. 13 is a front elevational view of the FIG. 2 embodiment positioned on an accident victim and showing the frontal region strap secured to its attachment point.

So that a wearer of the appliance may be ventilated with an oxygen mask or the like, the facial area of a wearer is left unobstructed by the appliance (FIG. 13).

Whereas, not all individuals have the same body size, the embodiments 10 and 11 of the appliance may be of varying dimensions so as to allow for the safe and comfortable fit of any sized individual. Additionally, so that a health care provider may quickly locate the correct sized appliance each size may be formed of a different colored material.

In operation, one can readily and safely place the appliance 10 or 11 onto an accident victim 80 as shown by FIGS. 8, 9, 10, 11, 12, and 13.

FIG. 8 illustrates the appliance 11 having the draw strap 50, anterior cervical strap 66, axillary straps 34 and 36, and the frontal region strap 134 disengaged for positioning of the appliance 11 onto an accident victim 80.

FIG. 9 illustrates how the appliance 11 is brought from above and behind for positioning onto an accident victim 80.

Figure 11:
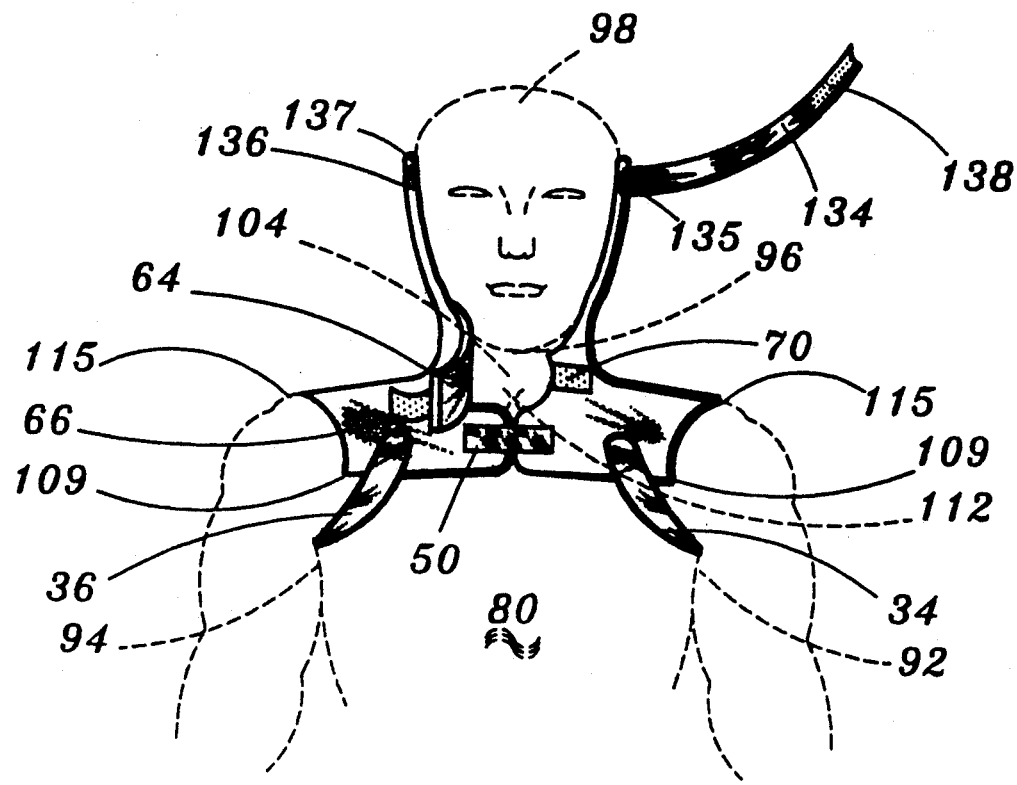
FIG. 11 is a front elevational view of the FIG. 2 embodiment positioned on an accident victim and showing the arm straps attached beneath the left and right armpits.
Figure 12:
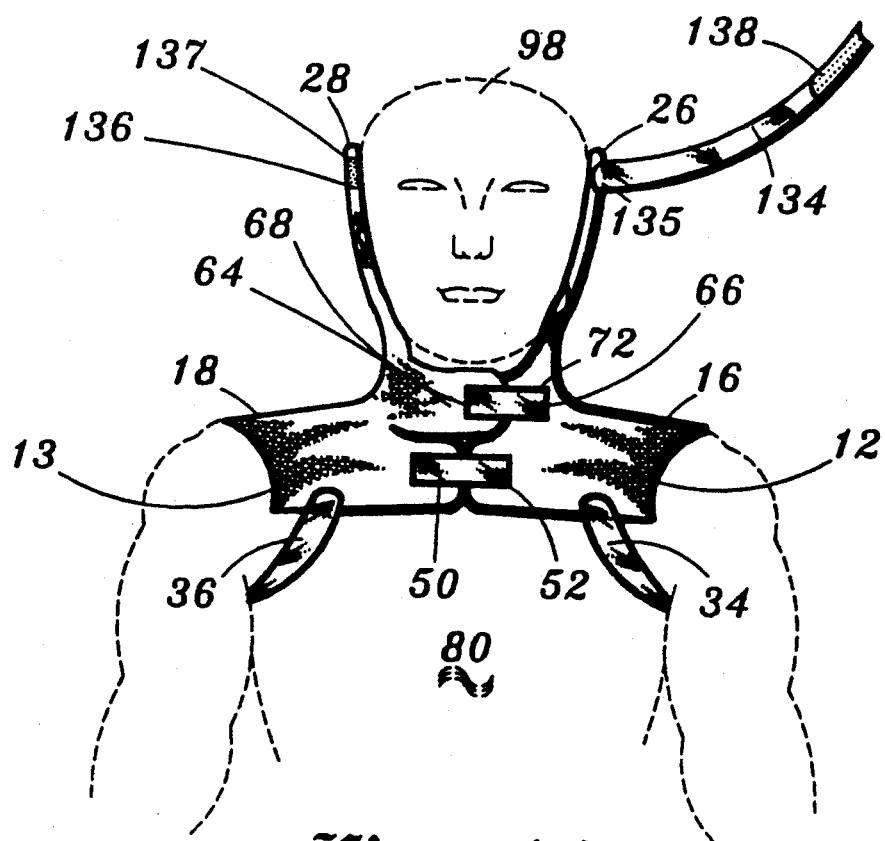
FIG. 12 is a front elevational view of the FIG. 2 embodiment positioned on an accident victim and showing the anterior cervical flap secured by the anterior cervical strap.

FIG. 10 illustrates how the draw strap 50 is secured first in order to immobilize the cervical rachis 125 (FIG. 14). The next step in positioning the appliance 11 onto an accident victim 80 is illustrated by FIG. 11 where the axillary straps 34 and 36 are utilized to draw the front and back portions together in order to add further shell rigidity. FIG. 12 illustrates the closed position of the anterior cervical flap 64.

FIG. 13 illustrates the final step in positioning the appliance 11 onto an accident victim 80, wherein the frontal region strap 134 is secured so as to completely immobilize the cervical rachis 125 of an accident victim.

An alternative preferred embodiment of the Cephalic and Cervical Support Apparatus 210 is shown in FIGS. 16–25 as including a semirigid, flexible unitary shell 212 having a facial opening 214 and upper, middle and lower sections 216, 218 and 220.

The upper section 216 is preferably formed to substantially conform to a wearer's head and encompasses the apparatus from the top of the chin and lower jaw support 234 to the top of the support apparatus 210. The upper section 216 contains the facial opening 214, which is adapted so as to leave the facial area unobstructed by the installed support appliance 210. The upper section 216 also includes a pair of ear openings 222a and 222b cut into and through opposite sides of the upper section 216 so that health care providers may obtain access to the ears of a wearer. The upper section 216 also includes a forehead strap 224 preferably releasably and adjustably mounted to the top forward portion 226a and 226b of the upper section 216. The forehead strap mounting means is preferably a hook and loop fastener mounted on each end of the strap 224, and on the outer face of the apparatus at the top forward portion 226a and 226b such that the strap 224 may be placed across an apparatus wearer's forehead and secured, thus further immobilizing the wearer's neck area. Importantly, the forehead strap 224 is designed to fit on and across the apparatus wearer's forehead in a substantially horizontal holding position, thus substantially eliminating downwards vertical pressure on the spine of the support apparatus wearer, which can be caused by angled forehead straps. The forehead strap 224 may also be constructed of the same material and attached the same way as disclosed in the previously submitted specification as reference numeral 134.

The middle section 218 is preferably formed to substantially conform to the wearer's neck area, encircling the neck area and having a division 230 formed in the front face of the middle section 218. The division 230 is one part of the shell division 229, which includes the divisions in the lower section 220 also. The division 230 is substantially vertical and extends downwards from the left bottom of a wearer's jaw area, towards and into the lower section 220. Underneath the chin of the apparatus wearer is preferably a chin and lower jaw support 234, consisting of an outward shell extension approximately ⅞" in extension and between 3½" and 4½" in width across the facial opening 214, in the preferred adult-sized embodiment of the present invention. This chin support 234 assists in further immobilizing the wearer's head, and in addition makes the apparatus more comfortable to wear.

Figure 22:
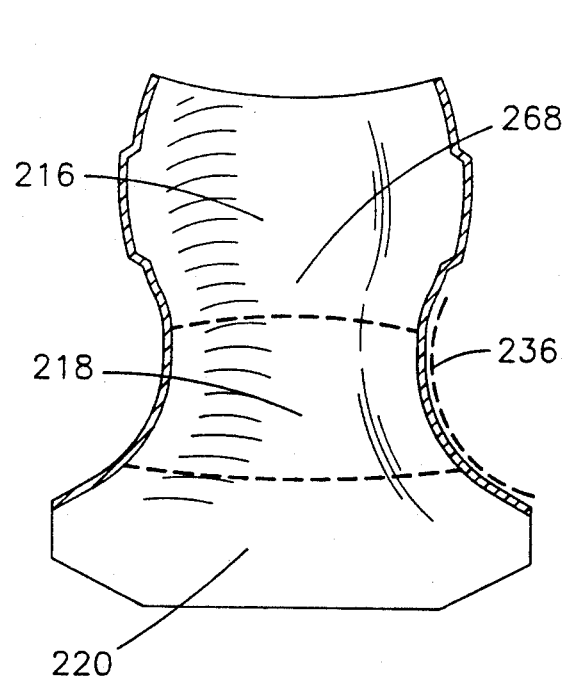
FIG. 22 is a front sectional view of the invention of FIG. 16 taken along line 23—23 in FIG. 19 showing the substantially form-fitting back and the concave joining curve extending along the upper, middle and lower sections of the invention.
Figure 23:
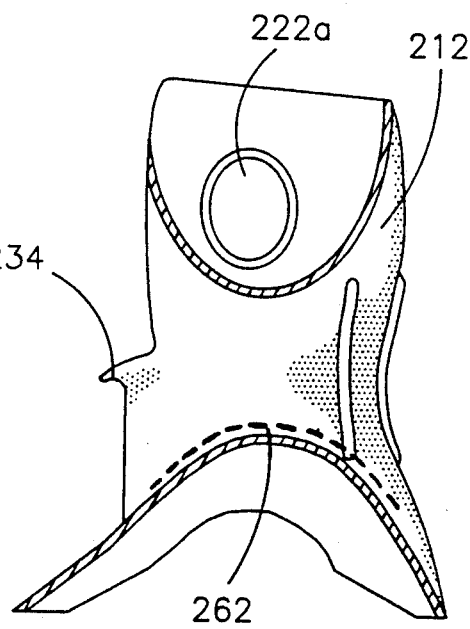
FIG. 23 is a side sectional view of the invention of the FIG. 16 taken along line 22—22 in FIG. 18 showing the side cutaway of the shell and the ear opening.
Figure 24:
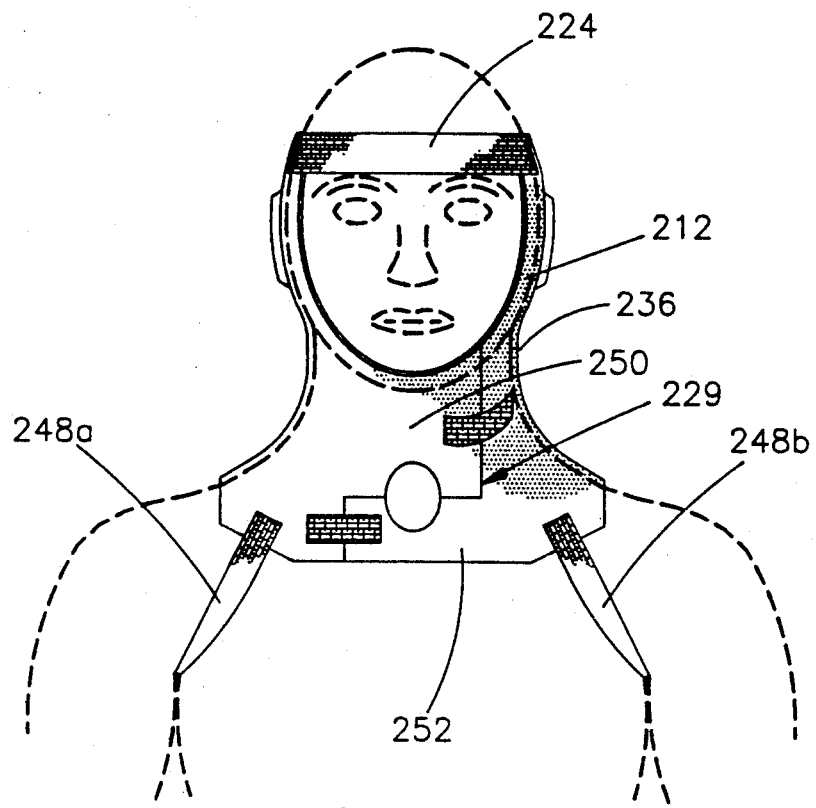
FIG. 24 is a front view of the support of FIG. 16 on a wearer showing how the joining curves conform to a wearer's neck, head, shoulders and chest and how the arm straps secure the device on the wearer.
Figure 25:
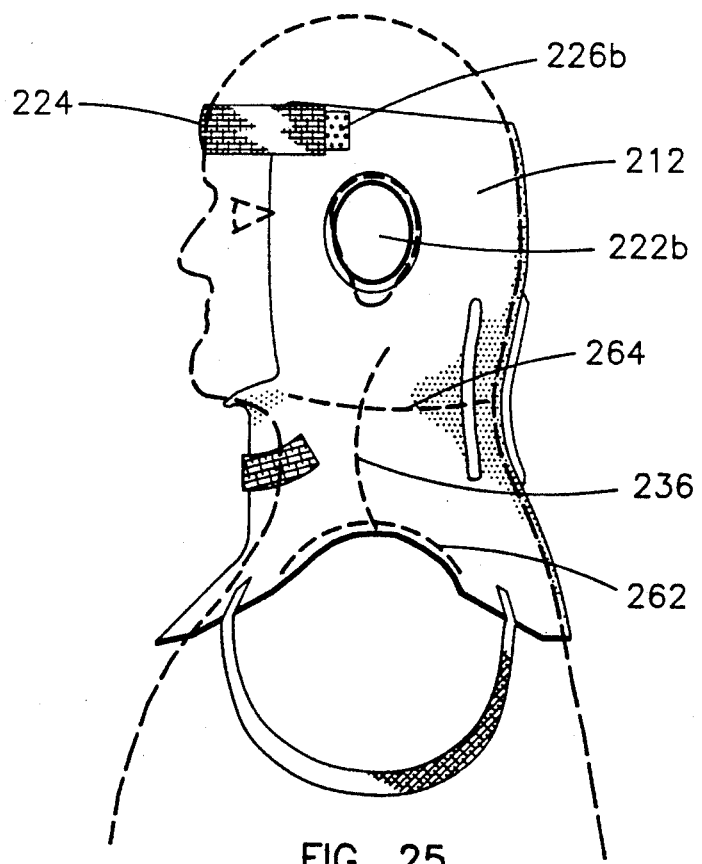
FIG. 25 is a side view of the support of FIG. 16 on a wearer showing the horizontal forehead strap and the chin and lower jaw support position.

On all sides of the middle section 218, except for the front face 232, a convex joining curve 236 is formed by the joining of the upper, middle and lower sections 216, 218 and 220. This joining curve 236 is best shown in FIG. 22 as a cutaway side of the shell 212, as extending downwards from just below the ear openings 222a and 222b to the outer edges of lower section 220.

This curve 236 adds stability to the shell 212 and helps the shell 212 conform to the head, neck and shoulder contours better. Furthermore, the convex joining curve 236 allows for a more comfortable wearing of the apparatus 210, which is important for situations in which the apparatus 210 may be worn for extended periods.

Beginning between 1" and 3", preferably 2", below the lowest part of the chin and lower jaw support 234 is the lower section 220 of the apparatus 210, which is formed to substantially conform to an apparatus wearer's upper shoulder back and chest area and to rest thereon. The lower section 220 is between 10" and 13", and preferably 11", in width at the widest point in the transverse dimension shown by line 21—21 in FIG. 18.

The lower section 220 contains a division 238 which is a continuation of the division 230 in the middle section 218. The lower section division 238 preferably has two components, a horizontal one 240 and a vertical one 242. The horizontal division 240 extends rightwardly from the end of the vertical division 230 in the middle section 218, extending beneath the chin and lower jaw support 234, between 2" and 4", and preferably 3", below that support 234. The horizontal division 240 extends approximately 3" to 5" across the front face 246 of the lower section 220, approximately the same width as the chin and lower jaw support 234. The horizontal division 240 then intersects the vertical division 242 in the lower section 220, which extends downwards to the base of the lower section 220. The Z-shaped shell division 229 thus formed results in two flaps being formed, an upper neck flap 250 and a lower chest flap 252. In this manner, the shell 212 can be opened to allow the support apparatus 210 to be installed on a wearer.

Figure 17:
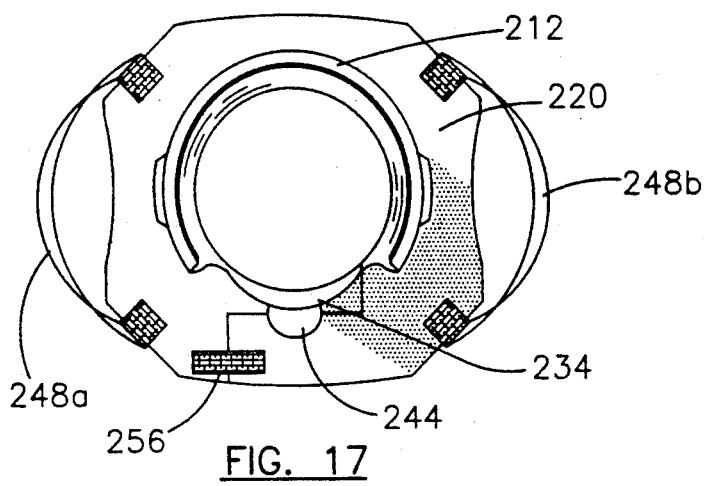
FIG. 17 is a top plan view of the invention of FIG. 16 showing the head opening and the middle concave curve conforming to the neck area.
Figure 18:
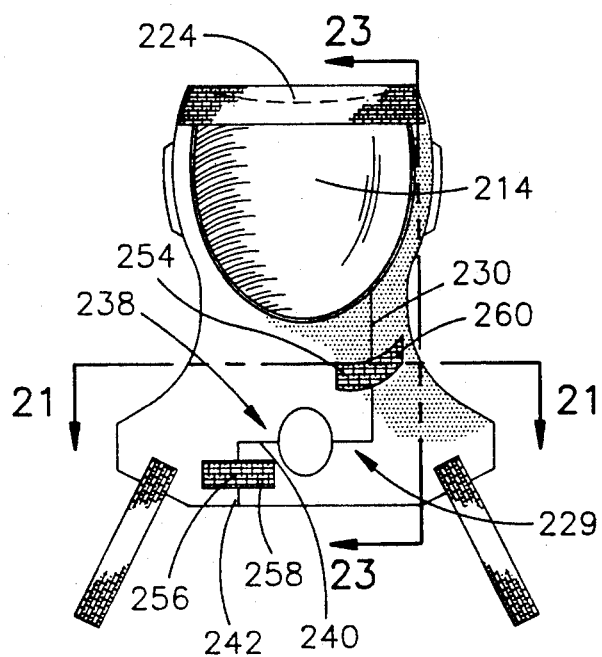
FIG. 18 is a front elevational view of the invention of FIG. 16 showing the division in the front of the shell and the hook and loop fasteners for securing and closing the division and the concave side curves of the shell.
Figure 19:
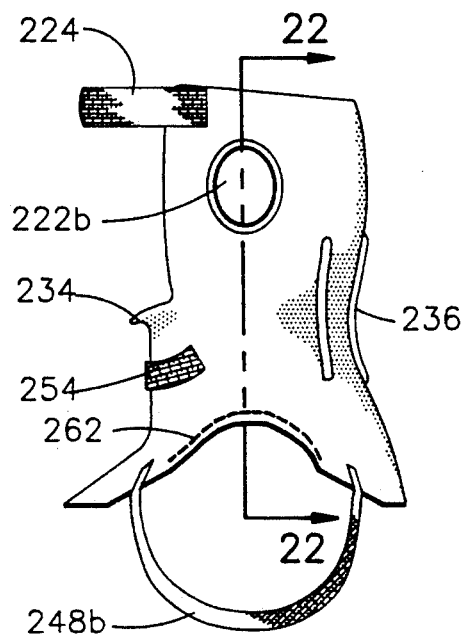
FIG. 19 is a side elevational view of the invention of FIG. 16 showing the rear joining concave curve.
Figure 20:
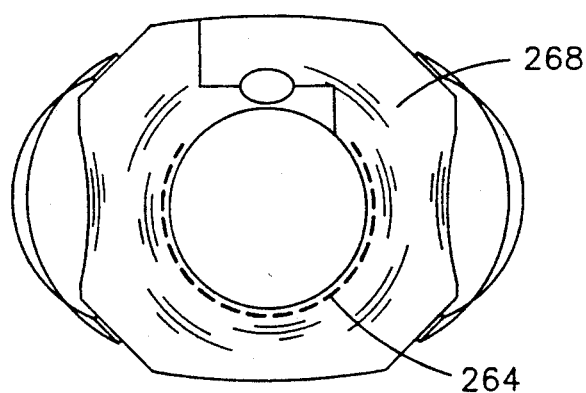
FIG. 20 is a bottom plan view of the invention of FIG. 16.
Figure 21:
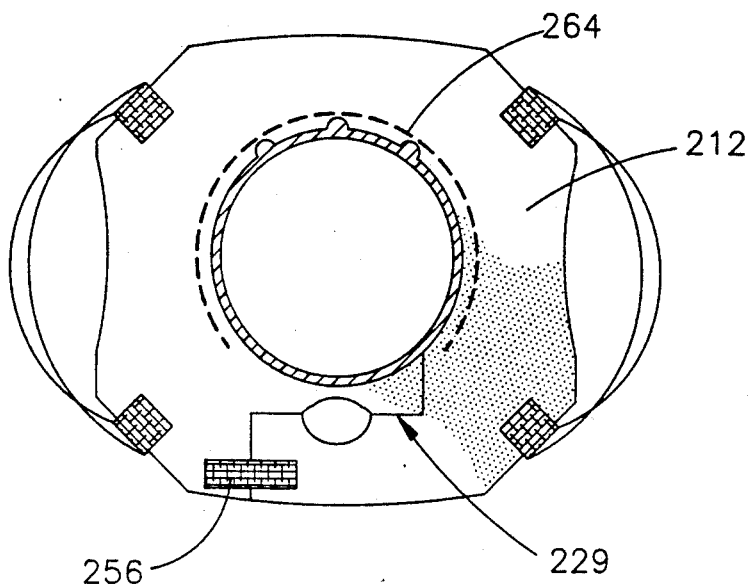
FIG. 21 is a top sectional view of the invention of FIG. 16 taken along line 21—21 in FIG. 18 showing the lower part of the middle section and the lower section.

Also mounted on the lower section 220 are a pair of arm straps 248a and 248b preferably made of an elastic material. The arm straps 248a and 248b are mounted on opposite sides of the lower section 220, as shown in FIG. 17, the strap ends removably and adjustably attached to the base of the apparatus 210, thus forming loops. The arm straps 248a and 248b are preferably mounted and installed on a wearer as disclosed in the previously submitted specification as reference numerals 34 and 36.

Finally, a tracheotomy opening 244 may be formed in the front face 246 of the lower section 220 approximately centered both vertically and horizontally on the horizontal division 240. The tracheotomy opening 244 is preferably between 1¼" and 2¼" in diameter to allow access for health care workers to the neck area to perform tracheotomies and the like.

To close and secure the shell division 229, a pair of securement straps 254 and 256 have their ends permanently mounted on the flaps 250 and 252, the upper securement strap 254 on the upper neck flap 250, the lower securement strap 256 on the lower chest flap 252. Mounted on the shell 212 at points 258 and 260 are portions of loop fastener which may be engaged by hook fasteners mounted on the nonmounted ends of the securement straps 254 and 256, such that the shell division 229 may be closed and secured in various positions to accommodate variously sized wearers.

The lower section 220 also has a downwards facing lower concave curve shape 262 such that the shoulders and trapezius muscle area of a wearer may fit therein.

The middle section 218, furthermore, has a middle concave curve 264 extending rearwardly in a substantially horizontal plane from a side of the front face of the middle section 218, curving around the side and rear neck area of a wearer, and ending in the opposite side of the front face.

The three curves previously mentioned, the convex joining curve 236, the downwards facing lower concave curve shape 262 and the middle concave curve 264, as a group work to greatly increase the stability of the support apparatus 210 in the following manner. As shown best in FIG. 25, the three curves 236, 262, 264 are in substantially orthogonal planes therefore providing tensioning strength in all directions. It is this unique combination of three curves 236, 262, 264 which further strengthens and reinforces the support apparatus 210.

The preferred construction material for the shell 212 is a pliable closed cell foam, which is a synthetic polymer. The synthetic polymer is preferably a polyurethane foam, and the shell 212 can be formed by layering the polyurethane foam one wearer-shaped mold. The layering of the foam results in increased rigidity of the shell 212. Preferably, the shell 212 is of a thickness between 1/32" and ¼", to keep the shell 212 semirigid but allow it to remain flexible.

Figure 26:
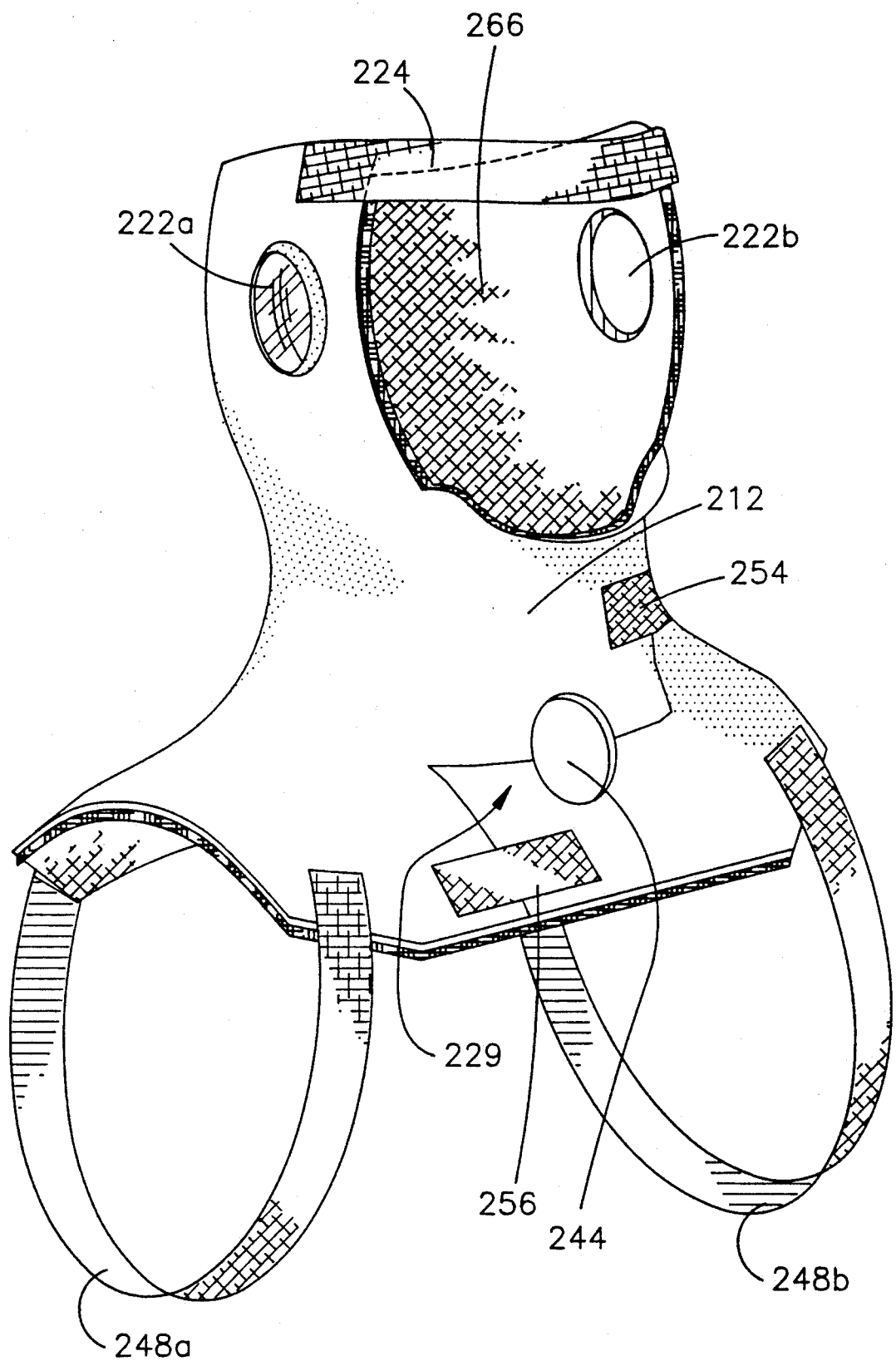
FIG. 26 is a perspective view of the support of FIG. 16 showing the shell liner installed in the shell.

A further preferred element of the present invention is a shell liner 266 as shown in FIG. 26. The shell liner 266 may be formed from a variety of cushioning materials, among which may be a cotton-like fabric such as that used in cloth diapers or a closed-cell polymer sponge material such as any of a number of commercially available foam sponge materials. The shell liner 266 is designed to conform to the inner surface 268 of the shell 212 and to substantially cover the inner surface 268 of the shell 212. The shell liner 266 may be removably secured to the inner surface 268 by double-sided adhesive tape or any other suitable means. The shell liner 266 serves several important purposes, one of which is to provide a cushioning substance so that the shell 212 may fit more comfortably and snugly on the wearer, thus providing better cephalic and cervical support. Most importantly, the shell liner 266 can be replaceable and disposable, thus allowing sanitary conditions to be better maintained. With today's increased concerns over blood-transmitted diseases, this disposable liner 266 addresses the present needs of health care providers in helping to prevent the spread of disease, a need unaddressed by previously disclosed devices.

Whereas, the invention has been disclosed in connection with a preferred embodiment thereof, it is apparent that many modifications, substitutions, and additions may be made thereto which are within the intended broad scope of the appended claims.

Thus, there has been described and shown a cephalic and cervical support apparatus which accomplishes at least all of the stated objects.

I claim:

1. A cephalic and cervical support apparatus for immobilization and traction of the cervical rachis, comprising a semirigid flexible unitary shell having a facial opening and upper, middle, and lower sections, said upper section formed to substantially conform to a wearer's head adjacent and behind said facial opening, extending upwards along the rear and sides of said head to an extent above the upper portion of the wearer's forehead and above the wearer's ears and conforming to the sides of the wearer's head, said middle section formed to substantially conform to a wearer's neck area, encircling said neck area with a division in the front face of said shell below said facial opening to allow placement of said shell on the wearer and extending from underneath the wearer's jaw area downwards to said lower section, said lower section formed to substantially conform to a wearer's upper shoulder, back and chest area and to rest thereon, a division in a front face of said lower section connected to said division in said middle section whereby said unitary shell may be opened to allow said shell to be placed underneath a wearer's head, neck and shoulders, said upper, middle and lower sections joined to form a unitary substantially convex joining curve along the sides and rear of said sections, a pair of arm straps connected to and extended forwardly between front and back portions of said lower section in nonintersecting spaced apart relation on opposite sides of said lower section whereby said shell may be securely anchored on said wearer, said upper section further comprising ear openings in and through the sides of said upper section, a forehead strap releasably and adjustably mounted on said upper section at positions above said ear openings, extending between opposite sides of said upper section, whereby said forehead strap may be placed on and across the forehead of a support wearer in a substantially horizontal direction thereby substantially to eliminate downward vertical pressure on the wearer's spine by said strap and to leave the wearer's ears exposed for visual inspection, fastening means for releasably and adjustably closing and securing said division in said front face of said shell whereby a range of differently sized wearers may be accommodated.

2. The support of claim 1 wherein said division fastening means comprises hook and loop fasteners.

3. The support of claim 1 wherein said front face of said middle and lower sections further comprises an opening providing access to the anterior region of a support wearer to allow for tracheotomies and the like.

4. The support of claim 1 wherein said lower section further comprises a downwards facing lower concave curve shape whereby the shoulders of a wearer may fit therein.

5. The support of claim 4 wherein said middle section further comprises a rear and side area having a middle concave curve to substantially conform to a wearer's neck.

6. The support of claim 5 wherein said convex joining curve, said middle concave curve, and said downwards facing lower concave curve combine to substantially increase the rigidity of said support, whereby said head and neck may be immobilized.

7. The support of claim 1 wherein the transverse dimension length of said lower section is between 10" and 13".

8. The support of claim 1 wherein said shell is formed of a pliable closed cell foam.

9. The support of claim 8 wherein said pliable closed cell foam is a synthetic polymer.

10. The support of claim 9 wherein said synthetic polymer is a polyurethane foam and wherein said shells are formed of multi-layer synthetic polymers.

11. The support of claim 1 wherein said shell is of thickness between 1/32" and ¼".

12. The support of claim 1 wherein said forehead strap comprises an elastic strap for further securing said head of said wearer of said support.

13. The support of claim 1 further comprising a shell liner to fit within and line the interior surface of said shell.

14. The support of claim 13 wherein said shell liner provides a cushioning substance whereby said shell may fit more comfortably and snugly on said wearer.

15. The support of claim 14 wherein said shell liner comprises a cotton-like fabric material.

16. The support of claim 14 wherein said shell liner comprises a closed-cell polymer sponge material.

17. The support of claim 14 wherein said shell liner is disposable and replaceable, whereby sanitary conditions may be better maintained.

18. A cephalic and cervical support for immobilization and traction of the cervical rachis, comprising
a first pliable shell open at the front and including
a back portion formed to be supported on the upper back and extend upwardly past the neck to at least the lambda region of the skull to secure the head against rearward movement,
right and left side portions extending forwardly from said opposite sides of the back portion to generally conform to the tops of a wearer's shoulders and sides of the head,
right and left front portions extending forwardly from said right and left side portions respectively for conforming to the anterior upper chest of the wearer and adapted to cover at least a portion of the area overlying a wearer's clavicles,
one of said front portions including an elongated neck stabilizer extended transversely toward the opposite front portion and shaped to conform to the chin and neck of a wearer to further secure the head,
a pair of arm straps connected to and extended between said back portion and said right and left front portions respectively to securely anchor said shell onto the wearer,
first fastener means for releasably and adjustably securing said right and left front portions together thereby to draw said back and side portions into engagement against the head of the wearer, and
second fastener means for releasably and adjustably securing said neck stabilizer to said opposite front portion, thereby to further conform said appliance to the full circumference of the wearer's head and to substantially fix the position of the head against both fore and aft rotational movement such that upon release of said second fastener means and opening of said neck stabilizer to expose a wearer's anterior cervical region, said right and left front portions and said first fastener means are operative to maintain immobilization and traction of the cervical rachis.

19. A cephalic and cervical support apparatus for immobilization and traction of the cervical rachis, comprising
a semirigid flexible unitary shell having a facial opening and upper, middle, and lower sections,
said upper section formed to substantially conform to a wearer's head adjacent and behind said facial opening, extending upwards along the rear of said head to a point above the upper portion of the wearer's forehead and conforming to the sides of wearer's head,
said middle section formed to substantially conform to a wearer's neck area, encircling said neck area with a division in the front face of said shell below said facial opening to allow placement of said shell on the wearer and extending from underneath the wearer's jaw area downwards to said lower section,
said lower section formed to substantially conform to a wearer's upper shoulder, back and chest area and to rest thereon, a division in a front face of said shell connected to said division in said middle section whereby said unitary shell may be opened to allow said shell to be placed underneath a wearer's head, neck and shoulders,
said upper, middle and lower sections joined to form a substantially convex joining curve along the sides and rear of said sections,
a pair of arm straps connected to and extended between front and back portions of said lower section towards opposite sides of said lower section whereby said shell may be securely anchored on said wearer,
a forehead strap releasably and adjustably mounted on said upper section, extending between opposite sides of said upper section, whereby said forehead strap may be placed on and across the forehead of a support wearer in a substantially horizontal direction thereby substantially to eliminate downward vertical pressure on the wearer's spine by said strap,
fastening means for releasably and adjustably closing and securing said division in said front face of said shell whereby a range of differently sized wearers may be accommodated,
said division in said shell being substantially sideways z-shaped, said neck portion having a substantially vertical division section on a side of the submandibular area, connected to a substantially horizontal division section extending across the top section of said lower section, connected to a substantially vertical division in said lower section beneath the opposite side of said submandibular area whereby an upper neck flap and an adjacent lower chest flap are formed.

20. A cephalic and cervical support apparatus for immobilization and traction of the cervical rachis, comprising a semirigid flexible unitary shell having a facial opening and upper, middle, and lower sections, said upper section formed to substantially conform to a wearer's head adjacent and behind said facial opening, extending upwards along the rear of said head to a point above the upper portion of the wearer's forehead and conforming to the sides of wearer's head, said middle section formed to substantially conform to a wearer's neck area, encircling said neck area with a division in the front face of said shell below said facial opening to allow placement of said shell on the wearer and extending from underneath the wearer's jaw area downwards to said lower section, said lower section formed to substantially conform to a wearer's upper shoulder, back and chest area and to rest thereon, a division in a front face of said shell connected to said division in said middle section whereby said unitary shell may be opened to allow said shell to be placed underneath a wearer's head, neck and shoulders, said upper, middle and lower sections joined to form a substantially convex joining curve along the sides and rear of said sections, a pair of arm straps connected to and extended between front and back portions of said lower section towards opposite sides of said lower section whereby said shell may be securely anchored on said wearer, a forehead strap releasably and adjustably mounted on said upper section, extending between opposite sides of said upper section, whereby said forehead strap may be placed on and across the forehead of a support wearer in a substantially horizontal direction thereby substantially to eliminate downward vertical pressure on the wearer's spine by said strap, fastening means for releasably and adjustably closing and securing said division in said front face of said shell whereby a range of differently sized wearers may be accommodated, said division in said shell being substantially sideways z-shaped, said neck portion having an upright division section on a side of the submandibular area, connected to a transverse division section extending across the top section of said lower section, connected to an upright division in said lower section beneath the opposite side of said submandibular area whereby an upper neck flap and an adjacent lower chest flap are formed.

21. The cephalic and cervical support apparatus of claim 20 wherein said fastening means comprises separate upper securement means on said upper neck flap and lower securement means on said lower chest flap such that upon opening of said upper neck flap to expose a wearer's anterior cervical region, said lower chest flap and lower securement means are operative to close said upright division in said lower section and to maintain immobilization and traction of the cervical rachis.

* * * * *